United States Patent [19]

Downs

[11] Patent Number: 5,291,785
[45] Date of Patent: Mar. 8, 1994

[54] METHOD AND APPARATUS FOR TESTING AN INFANT FOR HEARING DEFECTS

[75] Inventor: Marion P. Downs, Denver, Colo.

[73] Assignee: BAM World Markets, Inc., Englewood, Colo.

[21] Appl. No.: 767,002

[22] Filed: Sep. 27, 1991

[51] Int. Cl.$^5$ .............................. A61B 1/22; A61B 5/12
[52] U.S. Cl. ........................................ 73/585; 128/746
[58] Field of Search ................... 73/585; 128/746, 903

[56] References Cited

U.S. PATENT DOCUMENTS

| | | | |
|---|---|---|---|
| 3,938,500 | 2/1976 | Simmons | 128/746 |
| 4,007,731 | 2/1977 | Griffiths et al. | 128/746 |
| 4,139,730 | 2/1979 | Franklin | 73/585 |
| 5,023,783 | 6/1991 | Cohen et al. | 128/746 |
| 5,119,826 | 6/1992 | Baart de la Faille | 128/746 |

Primary Examiner—Hezron E. Williams
Assistant Examiner—Rose M. Finley
Attorney, Agent, or Firm—Francis A. Sirr; Earl C. Hancock

[57] ABSTRACT

An infant hearing test apparatus, primarily intended for use in the early detection of hearing problems of human infants in the birth to eighteen month age group, subjects an infant under test to two low intensity test sounds of an electronically filtered human voice in the frequency range of about 2000 to 4000 Hz. Of particular utility are the higher frequency sounds that are associated with the voice of a human female, for example a mother speaking a language dependent endearing term such as "Hi Baby", and a language independent sound to which the infant is sensitive, such as the sound of an infant crying. Both of these sounds are used to test the infant for body movement, for example head movement, with both sounds being reproduced at a relatively low intensity of about 46 dB and at a distance of about 12 inches from the infant. In the event that the infant does not respond to these low intensity sounds, a woman's voice is then used at a high intensity of about 90 dB SPL, and at a distance of about 3 inches, to further test the infant, in an attempt to elicit a reflex movement, such as an eye blink in response to this high intensity sound. These test sounds are digitally stored in a ROM in compressed data form.

10 Claims, 2 Drawing Sheets

METHOD AND APPARATUS FOR TESTING AN INFANT FOR HEARING DEFECTS

DESCRIPTION

1. Field of the Invention

The present invention relates to the field of hearing testing of humans, and more specifically to a hearing test apparatus and method that is primarily intended for use in the early detection of hearing problems in human infants, for example in the birth to eighteen month age group.

2. Background of the Invention

Hearing screening of human infants is not yet wide spread in either the physician's office or the home. Yet it is critical that hearing loss be identified and remedied as early as possible to ensure the highest development of an infant's language skills.

The infant brain is plastic and receptive to language learning mainly in the first two or three years of life. Yet there is a delay of generally two years in the diagnoses of congenitally deaf infants. When hearing losses are more moderate, the delay in diagnosis generally approaches four years.

The primary reason that physicians fail to screen infant hearing is that there has not been available an instrument with a well calibrated acoustic signal that incorporates frequency specific and attractive sounds suitable for identifying hearing loss in the young.

The method and apparatus of this invention provides an answer to this problem in that the invention is not only acceptable to physicians, but also is sufficiently simple to be used by parents.

It would be desirable for parents to be able to test their baby's hearing with a high degree of accuracy. In order to determine if this is a reasonable goal, a project was set up to determine whether parents are able to perform hearing screening, and to develop such an instrument.

In this study, 250 families were given a kit of noisemakers, and an instruction booklet graphically describing use of the noisemakers in screening the hearing ability of their children. Following screening trials, audiologists came to the homes and rated the parents' screening techniques. The audiologists then retested the children, first with the noisemakers, and then with a portable visual reinforcement (PVR) audiometer. Ambient noise measurements were also taken in the homes.

Eighty-eight percent of the parents demonstrated an acceptable screening technique, but only 5% used the noisemakers at an optimally soft level. Ambient noise levels of 60–75 dB during testing were considered responsible for unacceptable loud presentations by the parents.

This test however, produced no statistically significant differences between the parent's testing and the audiologist's testing. From this it can be concluded that parents are in fact able to screen their baby's hearing as well as audiologists can, but parents need a well controlled electronic instrument in order to screen accurately.

The present invention provides such an instrument.

Hearing screening procedures described in the art generally consist of two techniques: (1) With the baby seated on its mother's lap, a second testing individual kneels in front of the baby and extends an arm and a noisemaker low and to one side of the baby as the noisemaker is activated. The expected response from the baby is a turn of the head to the side where the noisemaker is located, and (2) One person visually shows the baby an attractive toy, while another person activates a noise from behind and to one side of the baby. The first person then observes whether the baby turned its head toward the sound.

The problem in these screening methods is that deaf children are visually alert, and can often out guess the testing procedure if there is the slightest visual clue as to where the sound is coming from. For example, a deaf child will see the extended arm moving, and will turn to see what is happening, or the deaf child will note that the second person has disappeared and will look around.

The present invention eliminates problems of this type by ensuring that the baby is aware of the testing individual on one side, and does not expect anything to happen on the other side. The testing individual then reaches around in back of the baby and sounds the audio stimulus of the invention on the back side of the baby, thereby misleading the baby as to where a sound could come from. In a study of the effectiveness of the invention about 60 presentations were made to deaf babies' ears, and only one head turn toward the sound occurred, this being a completely random head turn.

Attempts have been made to market electronic instruments that produce some variation of high frequency pure tone signals. These comprise generally two types: (1) high intensity warbled pure tone or narrow band instruments that identify severe deafness at birth or shortly thereafter, and (2) softer intensity pure tone instruments that are intended to identify milder hearing losses in children from birth to three years old.

For mild hearing loss in older children, as well as for severe hearing losses that might occur at or soon after birth, the most commonly used stimulus has been a "warble-tone", i.e. a pure tone that was "wobbulated" electronically. A 2000 Hz tone has been used in order to identify children who have a "nerve" hearing loss, this loss usually being more pronounced in the high frequencies than in the low frequencies.

The present invention operates upon the discovery that infants are much more attracted to the human voice than they are to the impersonal sound of a pure tone signal, however the signal is modified.

The problem of testing humans, including infants, for hearing loss has been addressed in the art.

The publication *Hearing in Children*, the second edition, copyright 1978, is of interest in that chapter 5 thereof contains a general discussion of "Clinical Audiologic Testing of Children". For example, at page 116 a table shows the "Auditory Behavior Index of Infants" and contains a "Noisemaker" and a "Startle to Speech" column. For example, at page 119 of this publication it is stated "toy noizemakers are the most useful signals" and at page 120 it is stated "Speech, pure tone, and noise audiometry through loudspeakers should be available --." Other testing parameters described in this publication include at page 118 the use of a 90 dB signal, at page 116 the use of a 40–60 dB signal, at page 117 isolation of the infant, at page 120 use of a 4,000 Hz signal at 25-35 dB at 3 inches distance, adt page 120 use of a 1,000 Hz signal 45-55 dB at 3 inches distance, at page 120 use of a loud noize of 50-85 dB, and at page 116 speech at 65 dB.

U.S. Pat. No. 3,799,146 describes an arrangement wherein a series of test tones, of different levels of loudness, or a musical composition, are played through earphones as the subject is monitored for brainwave activity.

U.S. Pat. No. 3,938,500 describes a procedure whereby a subject's motor activity is monitored in response to unexpected audio stimulus. A cribside sound level of between 92 and 93 dB SPL is suggested, and at a frequency in the 2 to 4 kHz band.

U.S. Pat. No. 4,132,226 describes measuring the auditory threshold of marine mammals.

U.S. Pat. Nos. 4,489,610 and 4,759,070 describe computerized audiometers that generate a sequence of tones in real world hearing situation, and are capable of programming a hearing aid, and components thereof, for use by the person being tested.

U.S. Pat. No. 4,847,763 describes an audiometer wherein test signals of selectable kind and intensity may be used from a repertoire that is contained on a digital disk.

While prior devices, such as is exemplified above, are generally useful for their intended purposes, the art fails to provide a simple and inexpensive apparatus and method that is useful by unskilled and relatively untrained adults in providing reliable testing of infants for hearing defects.

SUMMARY OF THE INVENTION

The present invention provides a method and an apparatus that is new, unusual and innovative in screening the hearing of human infants via behavioral observations of the infants. The apparatus of the invention presents unusual audio stimuli for hearing screening, namely, frequency filtered voice signals, preferably of a human female. The method consists of a mother, for example, displaying a toy in one hand in order to attract the baby's attention. The mother then reaches her other arm around the back of the baby, and uses the hand-held apparatus of the invention presents the above mentioned frequency filtered human voice audio stimulus.

The apparatus and method of the present invention uses the innovative stimulus of a filtered human voice that is most attractive to babies. The invention incorporates high frequency into the audio screening stimulus by filtering out the voice frequencies that are below about 2000 Hz, and more preferably the filtered screening stimulus lies in the 2000 to 4000 Hz band.

The audio stimulus of the invention is digitally stored in ROM chip of an apparatus constructed in accordance with the invention. The signals stored in ROM preferably include three audio stimulus, without limitation thereto, such as (1) a language independent sound such as a baby's cry that has been band pass filtered to eliminate frequencies other than those generally in the 2000–4000 Hz range, (2) a mother's voice saying a language dependent endearing term such as "Hi, Baby" that likewise has been filtered to produce a signal in the range of about 2000–4000 Hz, and (3) a woman's voice saying a language independent term such as "BUH-BUH-BUH-BUH-BUH".

The first two audio stimulus are reproduced, during the testing of the infant, at a relatively low intensity of about 46 dB SPL, and at a relatively long distance of about 12 inches from the infant undergoing test, for the purpose of identifying mild hearing losses in infants.

The third signal is reproduced at a relatively high intensity of about a 90 dB SPL level, and at a relatively short distance of about 3 inches, for the purpose of producing a reflex from the infant being tested, for example an eye blink. This high intensity test is conducted to corroborate findings that may have been made in testing the infant using the two above mentioned softer sounds, to thereby ensure that a deaf baby who has randomly turned to the softer sound will not be incorrectly labelled as having adequate hearing. It has been noted that a truly deaf baby will never give a reflex eye blink to this third high intensity sound.

These and other objects and advantages of the invention will be apparent to those of skill in the art upon reference to the following detailed description, which description makes reference to the drawing.

DETAILED DESCRIPTION OF THE INVENTION

Figure 1:
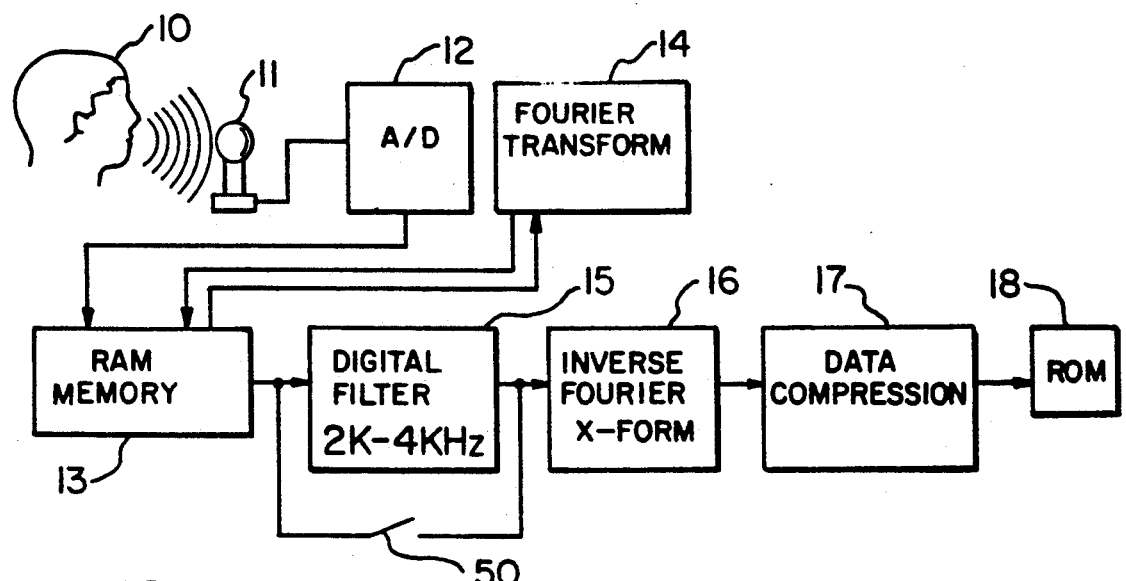
FIG. 1 is a showing of an apparatus and a method as it is used to load a read only memory (ROM) unit with sounds that are later used in the testing of human infants for hearing defects.

The apparatus and method of the present invention uses a high frequency, band pass filtered, human voice, preferably a female voice, that is most attractive to babies.

The sounds that are stored in a ROM chip preferably include a baby's cry that has been band pass filtered in the 2000–4000 Hz range. This audio stimulus is reproduced at a relatively low intensity of about 46 dB SPL, and at a relatively long distance of about 12 inches from the infant undergoing test, for the purpose of identifying a mild hearing loss.

Also included in this ROM chip is a mother's voice saying a language dependent endearing term such as "Hi, Baby". This audio stimulus is likewise filtered to produce a sound in the range of about 2000–4000 Hz. This sound is also reproduced at a low intensity of about 46 dB SPL, and at a distance of about 12 inches, for the purpose of identifying mild hearing losses.

The third sound stored in the ROM chip is a woman's voice saying a language dependent term such as "BUH-BUH-BUH-BUH-BUH". This sound is reproduced at a high intensity level of about 90 dB SPL, and at a L relatively close distance of about 3 inches, for the purpose of producing a reflex, such as an eye blink, it being known that a deaf infant who has randomly turned to one or both of the first two low intensity sounds will not give a reflexive eye blink to this third sound. Preferably this high intensity sound is not frequency filtered, to thereby provide a broad band of frequencies with the sound.

The first two above mentioned sounds are ones that an infant will naturally react to if the infant is able to hear the sounds. The basic needs that a child seeks to satisfy are believed to include pleasure, learning interest, and a natural curiosity. In accordance with the teachings of the present invention, the human voice is more effective in attracting the attention of infants than are pure or warbled tones. Voice sounds are familiar to the infant, and they are interesting to the infant because the infant is actively learning a language. Also, the human voice is associated with the pleasant interaction of the infant with parents, siblings, and other infants.

In the preferred implementation of the invention, the two low intensity sounds, such as a crying baby, and a woman's voice saying "Hi Baby", are reproduced at about 46 dB SPL at a distance of about 12 inches from the infant's ear.

The crying sound, in addition to being familiar to the infant, has the advantage of having a universal language content, i.e. it is language independent. The "Hi Baby" sound has the characteristic of being familiar, it has language content, and it is language specific, i.e. in this case it is specific to the English language. There are of course equivalent sounds or terms for all languages.

A screening sound in accordance with the invention must contain sufficient energy in a frequency band that is recognized as speech, after attenuation of all other speech frequencies below 2000 Hz in the audible range.

The frequency band selected in accordance with the invention is a band that is most degraded by a particular hearing disorder. For example, typical sensorineural hearing loss can be characterized by degraded hearing at higher frequencies, such as 2000 Hz and upward. Test sound frequencies below that range may be heard and responded to normally by an infant having a hearing loss.

The present invention uses frequency specific test sounds in order to obviate this problem, and in order to reliably facilitate the identification of a hearing loss in infants. Frequency specific human speech allows the infant hearing screening/monitoring instrument of this invention to yield improved sensitivity and specificity over other hearing screening instruments.

The high intensity sound of this invention is a term such as "BUH-BUH-BUH". This high intensity sound is used to test the infant for involuntary, reflex, eye blink response. The characteristic of this sound is its sudden onset at a high intensity level of approximately 90 dB SPL, and at a close distance of about 3 inches from the infant's ear. In this implementation, the sound is not filtered and thus provides a broader band of frequencies.

Figure 2:
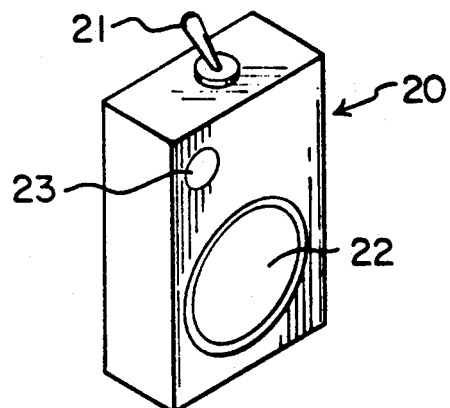
FIG. 2 shows an exemplary hand held case containing the ROM that is produced by operation of the apparatus and method of FIG. 1.

After the test sounds are selected in accordance with the invention, the sounds are processed by the apparatus of FIG. 1 in order to produce a ROM chip 18 for use in the hand held apparatus 20 of FIG. 2.

With reference to FIG. 1, the human voice of source 10, for example a female, speaks the selected sound into microphone 11. The amplified analog voltage from microphone 11 is digitized by analog-to-digital converter 12. The digital output of A/D 12 is stored as time domain signal in random access memory (RAM) 13.

The digitized and stored time domain signal in RAM 13 is now processed by network 14 by taking the fourier transform of the signal, in order to convert to the signal to the frequency domain. This frequency domain signal is then stored in RAM 13.

Next, band pass filtering, in a frequency range of from about 2000 Hz to about 4000 Hz, is performed by digital filter 15, followed by an inverse fourier transform operation by network 16, in order to convert the band pass filtered signal back to a time domain signal.

An optional data compression network 17 may now be used in order to reduce the memory size that is required for storing the time domain signal output of network 16.

The time domain signal, perhaps with data compression applied thereto, is now is stored in read only memory (ROM) 18.

At this point the digitized sound that is stored in ROM 18 is ready for electronic reproduction, as will be explained with reference to FIG. 3.

As noted above, when the high intensity signal is produced by source 10 digital filter 15 is not used, so as to produce a wide frequency band signal for storage in ROM 18. That is, digital filter 15 is bypassed by the use of switch 50.

All three of the above described sounds are now stored in ROM 18. In other embodiments of the invention, the language dependent sound(s) can be stored on one or more separate ROMs, such as 18, in order to expedite manufacture for use in different countries.

An exemplary electronic playback instrument in accordance with the invention was packaged in a leather or leather like case 20, shown in FIG. 2. Case 20 measures approximately 2.5 inches by ×4 inches by 1 inch, and is suitable for holding in the hand of a small adult.

Case 20 includes a button means 21 enabling the user to activate the test sounds that are digitally stored in ROM 18 of FIG. 1. Speaker 22 electronically reproduces these sounds in manner well known to those of skill in the art. A nine volt battery, shown in FIG. 3, may be used to power the electronics contained in case 20. A battery low indicator light 23 may be provided to warn the operator when the battery requires changing.

The method aspects of the present invention first ensures that the infant being tested is aware of the presence of the testing individual on one side of him. The infant is not distracted by the presence of a second individual in the vicinity of the infant. For example, the testing individual may play with the infant in order to get its attention. Thus the infant does not expect anything to happen on the other side of him. The testing individual then reaches around, generally to the back of the infant, while holding the apparatus of FIG. 2, and then sounds the audio stimulus that is contained in ROM 18, while the apparatus is held on the back side of the infant, thereby misleading the infant as to where a sound could come from.

Figure 3:
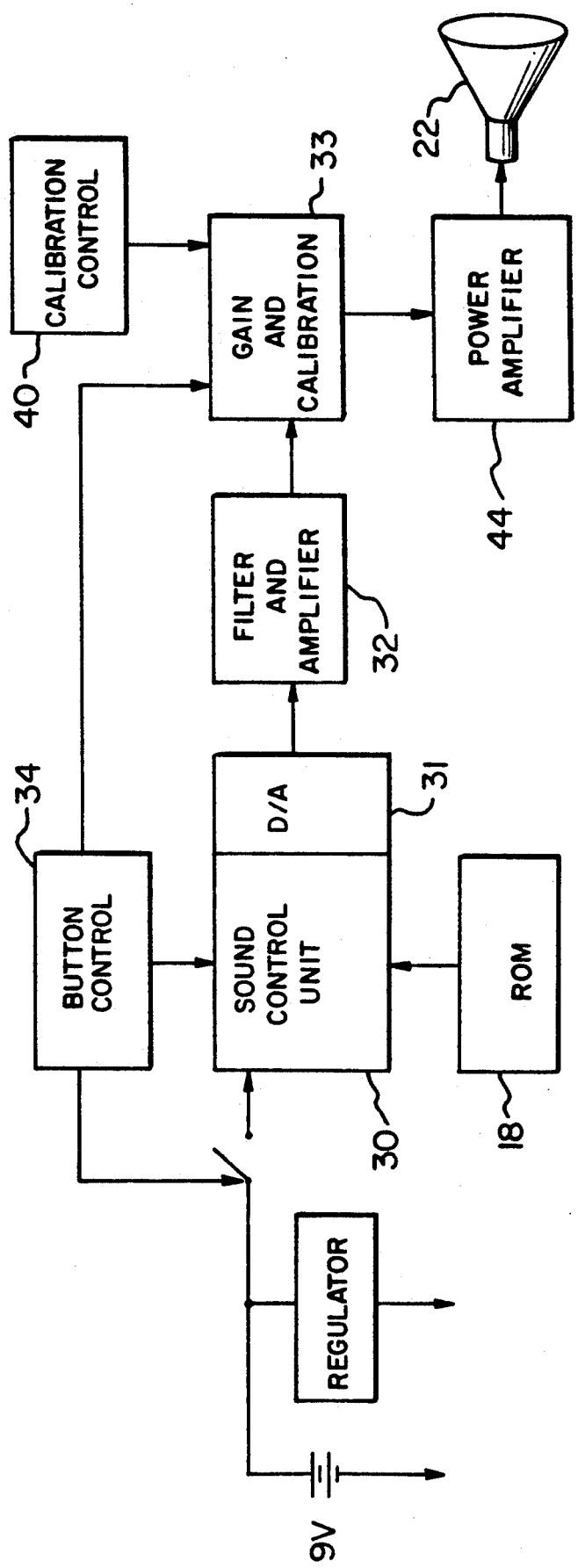
FIG. 3 shows the circuitry and logic within the apparatus of FIG. 2.

The electronic/logic of the apparatus of FIG. 2 is shown in FIG. 3. The electronic means of FIG. 3 is activated when control button means 34 is actuated. The functions that may be selectively activated by operation of push button means 34 are, (1) turn on the power, (2) cause sound control unit 30 to process the sound that is associated with the depressed button, and (3) select the gain for the sound that is associated with the depressed button.

Sound Control Unit 30 operates to retrieve the digitized sound data from ROM 18 in accordance with activation o control button means 34. If appropriate, the data from ROM 18 are then decompressed.

The digital signal from ROM 18 is now used to drive digital-to-analog converter (DAC) 31. The analog output signal from DAC 31 is preferably smoothed and amplified by filter amplifier 32.

The signal output from amplifier 32 is now attenuated by gain/calibration network 33, to thereby give a selected output sound amplitude, for example, either 46 dB SPL for a low intensity sound, or 90 dB SPL for a high intensity sound. Power amplifier 44 accepts the output of network 33 and operates to drive speaker 22.

Figure 4:
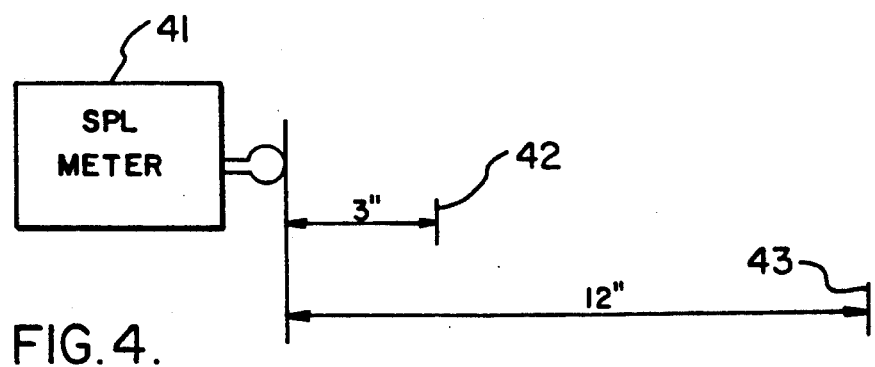
FIG. 4 shows the method whereby a sound pressure level (SPL) meter is used to calibrate the apparatus of FIGS. 2 and 3.

Sound output calibration of the apparatus of FIG. 3 is accomplished via calibration control 40, and by way of the procedure and apparatus shown in FIG. 4. A sound pressure level (SPL) meter 41 of a well known type is used to measure the sound output from speaker 22 of FIGS. 2 and 3. Meter 41 is used to measure the output of apparatus 20 using the A scale of the meter, and with the meter response set to slow. The peak reading of meter 41 is used to calibrate the apparatus of FIG. 3.

The high intensity sound output from speaker 22 is adjusted by the use of calibration control 40 so as to produce a high intensity sound of about 90 dB SPL from speaker 22 when apparatus 20 is located at physical position 42, about 3 inches from meter 41.

The low intensity sound output from speaker 22 is adjusted by the use of calibration control 40 so as to produce a low intensity sound of about 46 dB SPL from speaker 22 when apparatus 20 is located at position 43, a distance of about 12 inches from meter 41.

Ambient noise levels during the above described calibration should be generally less than 40 dB SPL.

The present invention uses frequency specific human voice test stimuli which provide an improvement over pure or warbled tones when screening an infant for hearing loss. The improvement results from the combination of the use of sounds that are interesting to the infant, and from the removal of certain frequencies from these sounds.

The invention teaches a new testing procedure that presents test sounds in a such a manner that the infant being tested is not given a visual indication of the presence of the test apparatus. This technique is accomplished by the testing individual being on one side of the infant, and reaching behind the infant to present the test stimulus on the other side of the infant.

Both language independent and language dependent test stimuli are provided in accordance with the invention. The "baby crying" sound is a universal, language independent, stimuli that can be broadly used in the testing of infant hearing. The language specific sound may utilize a mother's voice, in any language, in order to obtain a slightly more effective test.

While the present invention has been described with reference to preferred embodiments thereof, it is recognized that those skilled in the art will readily visualize yet other embodiments that are within the spirit and scope of the invention. Thus it is intended that the invention be limited solely by the following claims.

What is claimed is:

1. A method of testing a human infant for hearing defects by one testing individual using a sound producing testing apparatus, comprising the steps of;

gaining attention of an infant by operation of one hand of a testing individual, reaching a second hand of said testing individual back of the said infant, as said second hand holds said testing apparatus containing a number of sounds stored therein, said testing individual moving said testing apparatus to a relatively long distance from said infant's ears and activating a relatively low intensity sound from said testing apparatus, said sound having characteristics of interest to said infant and being language independent, and observing said infant for a responsive thereto, and said testing individual moving said testing apparatus to a relatively close distance from said infant's ears and activating a relatively high intensity sound from said testing apparatus, said second sound having characteristics of a type known to produce reflex movement in an infant that is not deaf and being language dependent.

2. The method of claim 1 wherein said low intensity sound is filtered to contain only sounds in about the 2 to 4 Khz frequency range, and wherein said high intensity sound is of an unfiltered broad frequency range.

3. The method of claim 2 wherein said low intensity sound is about 46 dB at the ears of said infant, and wherein said high intensity sound is about 90 dB at the ear of said infant.

4. The method of claim 3 wherein said relatively long distance is about 12 inches, and wherein said relatively close distance is about 3 inches.

5. The method of claim 1 including the step of said testing individual activating a second relatively low intensity sound from said testing apparatus at a relatively long distance from said ears of said infant, said second sound having the characteristics of being of interest to said infant and being language dependent, and observing said infant for a response thereto.

6. The method of claim 5 including an initial step of isolating said infant from others than said testing individual.

7. The method of claim 6 wherein said two low intensity sounds are filtered to contain only sounds in about the 2 to 4 Khz frequency range.

8. The method of claim 7 wherein said high intensity sound is of an unfiltered broad frequency range.

9. The method of claim 8 wherein said two low intensity sounds produce a sound intensity of about 46 dB at said ears of said infant, and wherein said high intensity sound produces a sound intensity of about 90 dB at said ears of said infant.

10. The method of claim 9 wherein said relatively long distance is about 12 inches, and wherein said relatively close distance is about 3 inches.

* * * * *